United States Patent
Zika et al.

(10) Patent No.: US 6,496,596 B1
(45) Date of Patent: Dec. 17, 2002

(54) METHOD FOR DETECTING AND CATEGORIZING DEFECTS

(75) Inventors: Steven J. Zika, Austin, TX (US); Christopher Lee Pike, Fremont, CA (US)

(73) Assignee: Advanced Micro Devices, Inc., Sunnyvale, CA (US)

( * ) Notice: Subject to any disclaimer, the term of this patent is extended or adjusted under 35 U.S.C. 154(b) by 0 days.

(21) Appl. No.: 09/274,212

(22) Filed: Mar. 23, 1999

(51) Int. Cl.[7] ................................. G06K 9/00
(52) U.S. Cl. ......................... 382/149; 700/110
(58) Field of Search ..................... 382/145, 148, 382/149; 348/87, 126; 356/237.4, 237.5; 250/559.45, 559.05, 559.06; 700/110–121; 702/82, 159; 438/16

(56) References Cited

U.S. PATENT DOCUMENTS 5,173,719 A * 12/1992 Taniguchi et al. .......... 356/394

OTHER PUBLICATIONS

Anil Gandhi et al., An Examination of Empirically Derived Within–Die Local Probabilities of Failure, IEEE Symposium on Defect and Fault Tolerance in VLSI Systems, 1997, ISBN: 0–8186–8168–3, pp. 53–61.*

* cited by examiner

Primary Examiner—Brian Werner
(74) Attorney, Agent, or Firm—Eschweiler & Associates, LLC

(57) ABSTRACT

A defect categorization method is described. Two or more regions are defined on a die. These regions can be repeated for other dies on the same wafer or corresponding regions on other dies on other wafers. The wafer(s) are scanned for defects. The location of each defect, along with any other desired defect data is stored. The stored defect data is then categorizing by region or regions within a die. As a result of the categorization, optional defect generation predictions can be made or optional yield or kill ratio predictions can be made. Also, specific regions(s) can be rescanned based on the result of the categorization.

14 Claims, 2 Drawing Sheets

METHOD FOR DETECTING AND CATEGORIZING DEFECTS

FIELD OF INVENTION

The present invention relates generally to categorizing defect based on user defined regions, also called bins.

BACKGROUND OF THE INVENTION

During fabrication process of solid state devices, such as a semiconductor devices, photomasks and reticles are used to form patterns of each layer of the devices on the wafer. Even an extremely small defect could greatly affect the production yield, circuits reliability or circuits functionality. For these reasons, wafers are inspected, often during the fabrication process upon completion of each step. A die, also called a chip, is a single square or rectangular piece of semiconductor material into which a specific electrical circuit has been fabricated. A single wafer normally has many dice. It may be desirable to have two or more different die patterns repeated on the same wafer.

Currently, defect in a die are detected, however, they are not categorized by user defined regions, nor are the defects analyzed based on those regions. A recognized problem, therefore, is detected defects are not automatically categorized by region to aid in defect analysis.

SUMMARY OF THE INVENTION

The aforementioned problems are solved by providing a method of categorizing detected defects based on user definable regions. Such user definable regions can be based on pattern density or other criteria.

BRIEF DESCRIPTION OF THE DRAWINGS

The present invention is described with reference to the accompanying figures. In the figures, like reference numbers indicate identical or functionally similar elements. Additionally, the left-most digit(s) of a reference number identifies the figure in which the reference number first appears.

DETAILED DESCRIPTION

Figure 1:
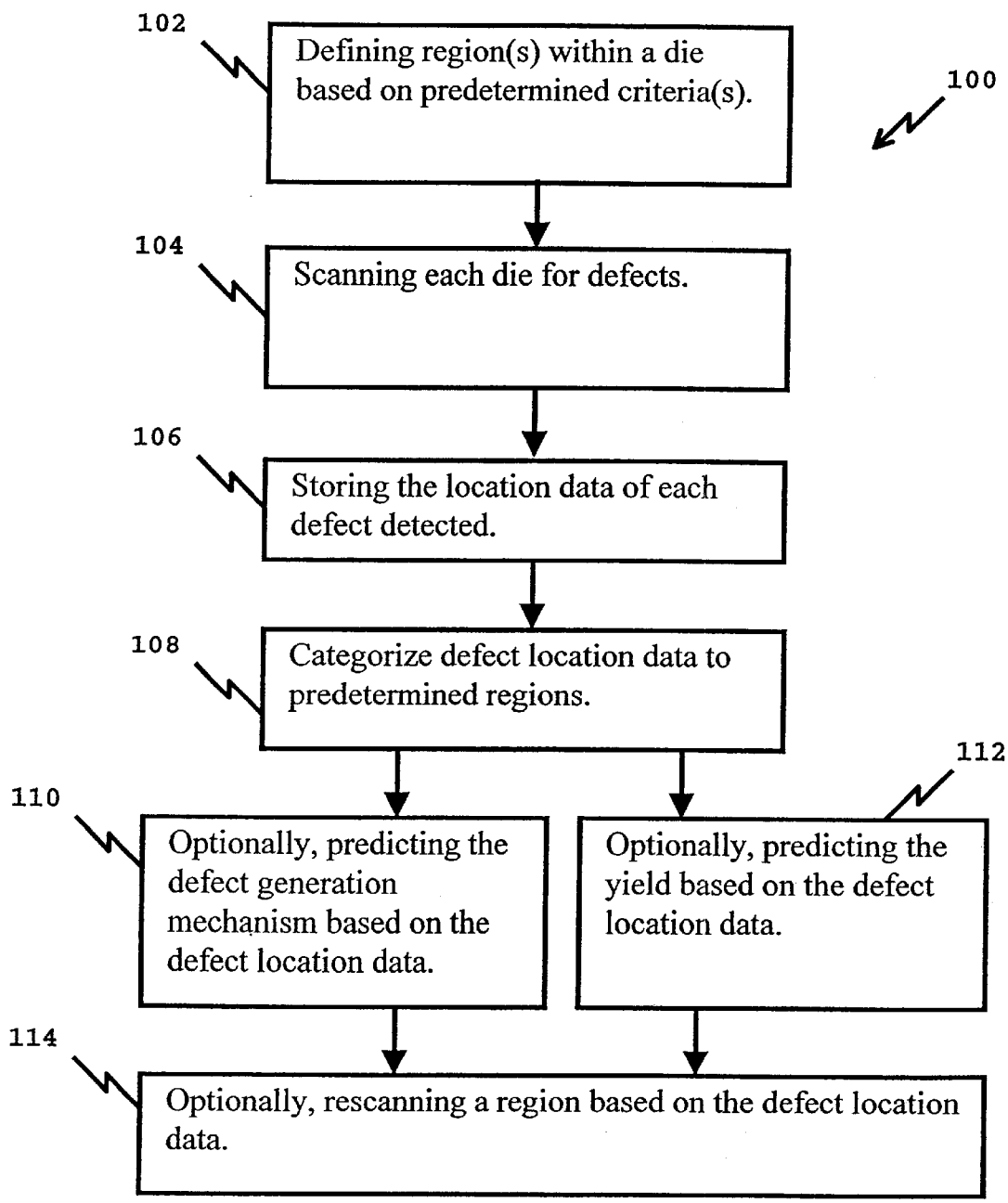
FIG. 1 is a flow diagram illustrating an embodiment of the method for detecting and categorizing defects.

Referring to FIG. 1, a process 100 for detecting and categorizing defects in a die on a wafer is illustrated. Process 100 can be used with a variety of semiconductor processing steps including lithography, which includes photolithography, x-ray lithography, and others, and etching, thin film deposition, and chemical mechanical processing. The process 100 can be repeated after any of the steps in wafer manufacturing process. When the process 100 is repeated after different steps, the user defined regions (described below) for each step may vary from the previous or subsequent steps.

At step 102, one or more regions(bins) on a die are defined. The regions are used for each identical die on the wafer. If more than one type of die are on the wafer, then each die type may have their own regions. Regions may correspond to regions on the die with high, medium, or lower pattern density. Alternatively, regions may correspond to areas on the die with specific device functional blocks, or other criteria such as physical location on the die (e.g. left or right, top or bottom). On a single die, there may be multiple regions defined by the same or different criteria. That is, a region on a die may correspond to a high pattern density area and an other region may correspond to a specific device functional block. The region's shape may be a regular shape, an irregular shape, or other shape. A region may include two non-continuos areas. A region may overlap an other region or regions. A region can be completely within an other region. A region can include the entire die. Alternatively, not all of the die need by within a region. That is, only a portion of the die may be scanned for defects.

At step 104, each die on the wafer is scanned for defects. One or more scanning techniques can be used to detect defects. Optionally, the sensitivity of the scan or the type of scan can be varied based on the region being scanned. Also, the sensitivity of some scanning techniques are inherently more or less sensitive in regions of high device density or low device density.

At step 106, the location of the defects detected in step 104 are stored for later processing. The defects can be store in memory, on a hard disk, or in any other media. The defect location data can include the coordinates within the die, the die location or other die identification data, and other location data. The location data may also be coordinates within the wafer. Also, location data can include the type of defect detected at each location or other data related to the defect.

At step 108, the defect locations stored in step 106 are categorized to the regions defined in step 102. The categorization may be a count of how many defects are detected in each region for all the dice on the wafer; a count of how many of each type of defect is detected in each region on the wafer, or other computations. Other defect related data may also be collected such as size of the defect, shape of the defect, and other. At step 108, the defect data is, categorized by which region or regions the defect is located in. Depending on the configuration of the regions defined in step 102, a defect may be in one, two, or more regions. Also, a defect may be detected that is not in a region. Such a defect may be ignored by process 100.

At step 110, the categorized defect location data is optionally used to predict the cause of the defects. That is the defect mechanism is determined based on an analysis of the defect location data and other related data. Because some defect types are sensitive to the structure, e.g. pattern density, a prediction of the cause of the defects can be made by analyzing the location, type and/or frequency of the defects. That is, if a first region is an area of high pattern density and more errors per unit of area are detected there, then the error can be classified as one that is sensitive to the structure.

At step 112, a yield prediction analysis is optionally performed where a predicted-yield is determined based on the defect location data. Since some defects are less likely to adversely affect the yield, the inverse of the "kill ratio," those defects are given less weight when determining a predicted yield. Also, analysis of defect density can be performed for each region independently. Thus, a more descriptive defect density profile can be determined for the die. Also, the defect density profile of different die can be analyzed to determine systematic defect mechanisms. Steps 110 and 112 can both be performed on the same die if desired.

At step 114, a portion of the die is optionally rescanned based on the defect location data. For example, if a high defect density was detected in a regions, the region can be rescanned to confirm the defect density or a more accurate or different scanning technique can be used to verify and categorize the defects.

The process 100 provides a superior method of categorizing defects in dice on a wafer because different sources cause different defects to occur at various rates in the various user defined regions. Thus, by analyzing defects by region within the die, information per region is available to determine the cause of those defects.

Figure 2:
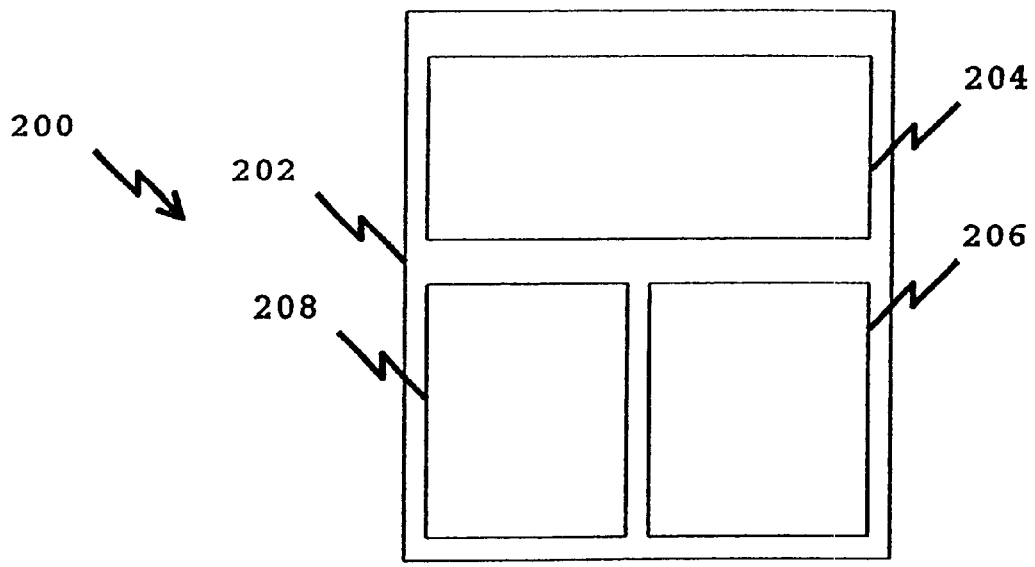
FIG. 2 is a diagram illustrating a die on a wafer with a first, second and third regions indicating user definable regions.

Referring to FIG. 2, a die 200 is illustrated. A wafer (not shown) includes at least one die and more commonly includes many identical dice repeated in a regular pattern.

In FIG. 2, the die 200 includes the outer edge of the die 202, a first region 204, a second region 206, and a third region 208. The regions define areas (bins) based on a characteristic of those regions. For example, the first region 204 may correspond to an area of high device density, while the second region 206 may correspond to an area of medium device density, and the third region 208 may correspond to an area of low device density. While three regions are used for illustration, any number of regions can be used. A region can include the periphery of the die and between the physical structures such as region 202 not including regions 204, 206, and 208. Such a region may be useful in distinguishing the non-critical errors, which only affect or primarily affect the periphery, from the critical errors, which affect the logic. As described above, these regions can be of any desired shape including regular shapes, irregular shapes, and a region can be non-continuos. For example, two non-continuos regions may have high device density and thus they are defined as one region. Every area of the die need not be in a region and a single region can include the entire die.

Figure 3:
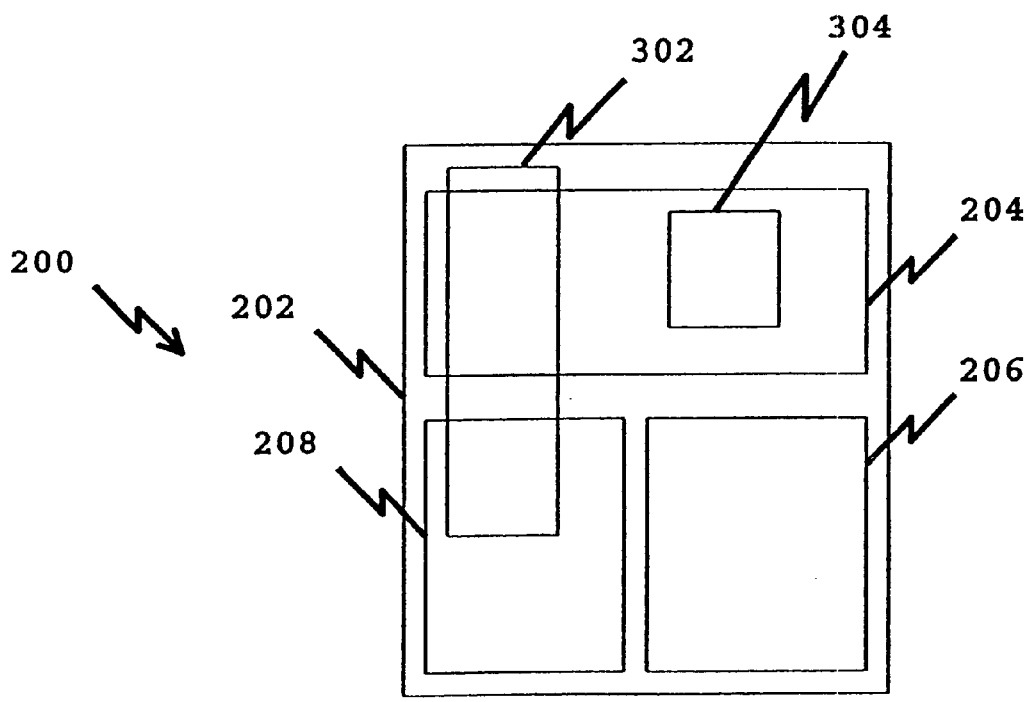
FIG. 3 is a diagram illustrating some variations of overlapping regions.

Referring to FIG. 3, regions 302 and 304 illustrate some alternative configurations of regions. Region 302 overlaps a portion of two other regions, 204 and 208. Region 304 is completely encompassed by region 204, that is it is a subset of region 204.

While preferred embodiments have been shown and described, it will be understood that they are not intended to limit the disclosure, but rather it is intended to cover all modifications and alternative methods and apparatuses falling within the spirit and scope of the invention as defined in the appended claims or their equivalents.

What is claimed is:

1. A method for monitoring defects in a die on a wafer, the die comprising a plurality of non-continuous functional areas, the defect monitoring method comprising:

(a) defining a first region in the die having a first pattern density range associated therewith, and comprising a plurality of the non-continuous functional areas, and a second region in the die having a second pattern density range associated therewith, wherein the first pattern density range is different than the second pattern density range and where the first and second regions are individually, user defined to take on any shape and size as defined by the user, and at any location on the die;

(b) scanning the die for any of a plurality of defect types and sizes;

(c) storing location data of each defect, wherein the location data comprises a die coordinate and a defect type;

(d) categorizing the stored location data of each defect with the first region and the second region wherein categorizing the stored location data comprises determining the number of each type of detected defect in each of the first and the second region, respectively; and (e) predicting a defect mechanism based on the categorizing in (d).

2. The method of claim 1, further comprising:

(f) predicting a die yield based on the categorizing in (d).

3. The method of claim 1, wherein the wafer includes a plurality of the die and the first and second regions of each die correspond to the same areas of each die, respectively.

4. The method of claim 3, wherein (d) includes categorizing defects from each die.

5. The method of claim 1, wherein (a) further comprises defining a third region that includes a portion of the first region, wherein the third region has a third pattern density associated therewith or comprises a unique functional block.

6. The method of claim 5, wherein the third region comprises a portion the first and second regions.

7. The method of claim 1, wherein the scanning in step (b) includes scanning using a plurality of scanning techniques.

8. The method of claim 7, wherein a first scanning technique is used in the first region and a second technique is used in the second region.

9. The method of claim 1, wherein the scanning of step (b) scans with a first sensitivity in the first region and a second sensitivity in the second region.

10. The method of claim 1, further comprising:

(e) predicting a die yield based on the categorizing step, wherein one type of defect is given less weight in predicting the die yield.

11. The method of claim 1, further comprising:

(f) predicting a die yield based on the categorizing step, wherein the predicting comprises analyzing categorized location data from multiple die with different patterns.

12. The method of claim 11, wherein the predicting comprises analyzing location data of regions with similar characteristics from multiple die with different patterns.

13. The method of claim 12, wherein the predicting includes compensating for the sensitivity of the scanning in each region.

14. The method of claim 1, further comprising:

(f) rescanning a region based on the defect location data.

* * * * *

UNITED STATES PATENT AND TRADEMARK OFFICE
CERTIFICATE OF CORRECTION

PATENT NO. : 6,496,596 B1 Page 1 of 1
DATED : December 17, 2002
INVENTOR(S) : Steven J. Zika and Christopher Lee Pike It is certified that error appears in the above-identified patent and that said Letters Patent is hereby corrected as shown below:

Column 1,
Line 12, please replace the word "devices" with the word -- device --.
Lines 46 & 47, please replace the word "regions" with the word -- region --.

Column 2,
Line 11, please replace the word "continuos" with the word -- continuous --.
Line 14, please replace the word "by" with the word -- be --.
Line 24, please replace the word "store" with the word -- stored --.
Line 39, please replace the word "other" with the word -- others --.
Line 57, please remove the hyphen between the words "predicted yield".

Column 3,
Line 3, please replace the word "regions" with the word -- region --.
Line 33, please replace the twice printed word "continuos" with the word
-- continuous --.

Signed and Sealed this

Thirteenth Day of May, 2003

JAMES E. ROGAN
*Director of the United States Patent and Trademark Office*